United States Patent
Contant et al.

(10) Patent No.: US 10,170,016 B2
(45) Date of Patent: Jan. 1, 2019

(54) COMPREHENSIVE MANAGEMENT OF HUMAN HEALTH

(71) Applicants: Olivier M. Contant, Redmond, WA (US); Christine V. Contant, Redmond, WA (US)

(72) Inventors: Olivier M. Contant, Redmond, WA (US); Christine V. Contant, Redmond, WA (US)

(*) Notice: Subject to any disclaimer, the term of this patent is extended or adjusted under 35 U.S.C. 154(b) by 830 days.

(21) Appl. No.: 14/636,031

(22) Filed: Mar. 2, 2015

(65) Prior Publication Data
US 2015/0170542 A1 Jun. 18, 2015

Related U.S. Application Data

(63) Continuation of application No. 12/693,219, filed on Jan. 25, 2010.

(51) Int. Cl.
| | | |
|---|---|---|
| *G16H 20/60* | (2018.01) | |
| *G09B 19/00* | (2006.01) | |
| *G06Q 10/10* | (2012.01) | |
| *G06Q 50/22* | (2018.01) | |
| *G06F 19/00* | (2018.01) | |

(52) U.S. Cl.
CPC .......... *G09B 19/00* (2013.01); *G06F 19/3475* (2013.01); *G06Q 10/10* (2013.01); *G06Q 50/22* (2013.01); *G06F 19/3481* (2013.01)

(58) Field of Classification Search
CPC ........ G06Q 50/22; G06Q 50/24; G06Q 10/10; G06F 19/322; G06F 19/323–19/327; G06F 19/30; G06F 19/34; G06F 19/3475; G06F 19/3481; G09B 19/00; G16H 10/00; G16H 20/00; G16H 20/30; G16H 40/00; G16H 40/40; G16H 40/60; G16H 40/63; G16H 40/67
USPC ........................................ 705/2, 3
See application file for complete search history.

(56) References Cited

U.S. PATENT DOCUMENTS

| | | | | |
|---|---|---|---|---|
| 5,142,358 | A * | 8/1992 | Jason ................. | A63B 71/0622 348/552 |
| 7,523,040 | B2 * | 4/2009 | Kirchhoff .......... | G01G 19/4146 128/921 |
| 2005/0143617 | A1 * | 6/2005 | Auphan ................... | A61B 5/08 600/26 |

(Continued)

OTHER PUBLICATIONS

Horizon Software International Introduces Healthy Child Campaign, Business Wire, Oct. 11, 2006, 3 pages.*

(Continued)

*Primary Examiner* — Jason S Tiedeman
(74) *Attorney, Agent, or Firm* — Payam Moradian

(57) ABSTRACT

A health guidance system receives health information from input devices and other sources, tracks one or more health goals, and enforces those goals by acting upon other devices. The health guidance system collects health information to paint a comprehensive picture of the user's health. The system uses the information it collects to interact with a variety of devices to enforce the user's health goals and ensure accountability. Thus, the health guidance system provides a comprehensive software system for collecting health information and using that information to produce positive changes in the health of users.

19 Claims, 4 Drawing Sheets

(56) References Cited

U.S. PATENT DOCUMENTS

| | | | | |
|---|---|---|---|---|
| 2005/0287502 A1* | 12/2005 | Southard | ............ | G09B 19/0092 434/236 |
| 2006/0218011 A1* | 9/2006 | Walker | .................... | G06F 19/00 705/3 |
| 2007/0098856 A1* | 5/2007 | LePine | .................. | A47G 21/02 426/231 |
| 2007/0191692 A1* | 8/2007 | Hsu | ...................... | A61B 5/4815 600/301 |
| 2008/0267444 A1* | 10/2008 | Simons-Nikolova | ........................ | A61B 5/1123 382/100 |
| 2008/0276461 A1* | 11/2008 | Gold | ...................... | A47G 21/02 30/142 |
| 2008/0281633 A1* | 11/2008 | Burdea | ................ | A61B 5/0002 705/2 |
| 2008/0311968 A1* | 12/2008 | Hunter | .................... | A63F 13/12 463/1 |
| 2009/0048493 A1* | 2/2009 | James | ..................... | G06F 19/00 600/300 |
| 2009/0099873 A1* | 4/2009 | Kurple | ................. | G06F 19/3475 705/3 |
| 2009/0113519 A1* | 4/2009 | Evans | .................... | H04N 7/162 726/1 |
| 2011/0125063 A1* | 5/2011 | Shalon | ................ | A61B 5/0006 600/590 |

OTHER PUBLICATIONS

Jancin, Bruce, Device allows adults to curb TV viewing, aid in obesity prevention: excessive Web surfing also a problem. Pediatric News 37.9: 37(1) (Sep. 2003).*

* cited by examiner

COMPREHENSIVE MANAGEMENT OF HUMAN HEALTH

CROSS-REFERENCE

The Present Application claims benefit to and is a continuation of U.S. application Ser. No. 12/693,219, filed on Jan. 25, 2010, which is incorporated herein by reference in its entirety.

BACKGROUND

Health is a constant concern for the human population. Even outside of specific diseases, healthy living can promote well being, energy, and a long life. Many people worry daily about weight management, proper exercise, proper diet, and other health related issues. Numerous government organizations (e.g., the World Health Organization and Center for Disease Control) and publications are dedicated to informing people about the role of their activities in increasing health and wellness. Many corporations have developed wellness programs to encourage workers to maintain or improve their health. Health encompasses physical, mental, and emotional factors and affects many areas of a person's life.

There are many existing methods for monitoring and improving health. Individual devices exist for measuring various indicators of health, such as heart rate monitors, blood pressure monitors, glucose tests, and so forth. Many devices exist that are related to fitness, such as exercise bicycles, treadmills, weights, and so forth. In addition, many systems exist for managing a person's diet, such as counting calories, the Atkins diet, and so forth. Some programs will send a person meals that are designed to deliver a specific amount of calories per day.

Unfortunately, overall health is difficult to track, and many existing systems integrate poorly with a person's lifestyle. For example, monitoring devices are only helpful if the person remembers to use them and record their results, diets are only as good as the person's discipline to follow the diet's rules, and other elements in a person's life may add to or detract from health that current systems do not track or consider at all. For example, the number of hours a day that a person watches television, whether the person drives or bicycles to work, and even the speed at which a person eats can all impact the person's health. In addition, even when useful health data is collected about a person, it is difficult for the person to act on that data. The person may invest significant hours learning about the number of calories best suited to that person's lifestyle, the amount of exercise that person needs, or the types of food he or she should eat.

DETAILED DESCRIPTION

A health guidance system is described herein that receives health information from input devices and other sources, tracks one or more health goals, and enforces those goals by acting upon other devices. Numerous devices can provide health input information. For example, classical devices, like pedometers, thermometers, and heart rate monitors, as well as newer devices, such as forks or spoons that measure bite count and/or food weight, mobile phone applications that monitor physical activity, sensing fabrics for monitoring physiological and biomechanical activities, and so forth. For the most part, this information is used only in the place it is collected and then lost. For example, a user may read the output of a heart rate monitor while jogging, make a quick decision to jog faster or slower, then discard the information. The health guidance system collects this information, such as on a central website or home computer, to paint a comprehensive picture of the user's health. Although some programs allow users to track health data, such as wellness websites where a user enters exercise or eating activity, these programs do little with the information other than making a few canned suggestions to the user (e.g., workout more, eat lower calorie foods). The health guidance system uses the information it collects to interact with a variety of devices to enforce the user's health goals and ensure accountability. For example, the system may interact with a television to deny the user the ability to watch television if the user has not exercised enough. These and other actions the system can take are described further herein. Thus, the health guidance system provides a comprehensive software system for collecting health information and using that information to produce positive changes in the health of users.

Unlike previous systems that, for example, might display a message on a web page (only when a user visited) giving the user health tips, the health guidance system takes an active, real-time role in the user's life. The system interacts with the user where the user is during the user's activities to influence the user to make healthy decisions. Like an accountability partner or a friend, the system is there with the user (through the devices that the user carries that are in communication with the system) to recommend healthy behavior, prevent bad behavior, and so forth at the time when the user needs it most. Although the system may include a website-based user interface, the user need not visit the website to gain the benefits of using the system. Rather, the system can push information to the user through text message, by programming device behavior, and so on.

Figure 1:
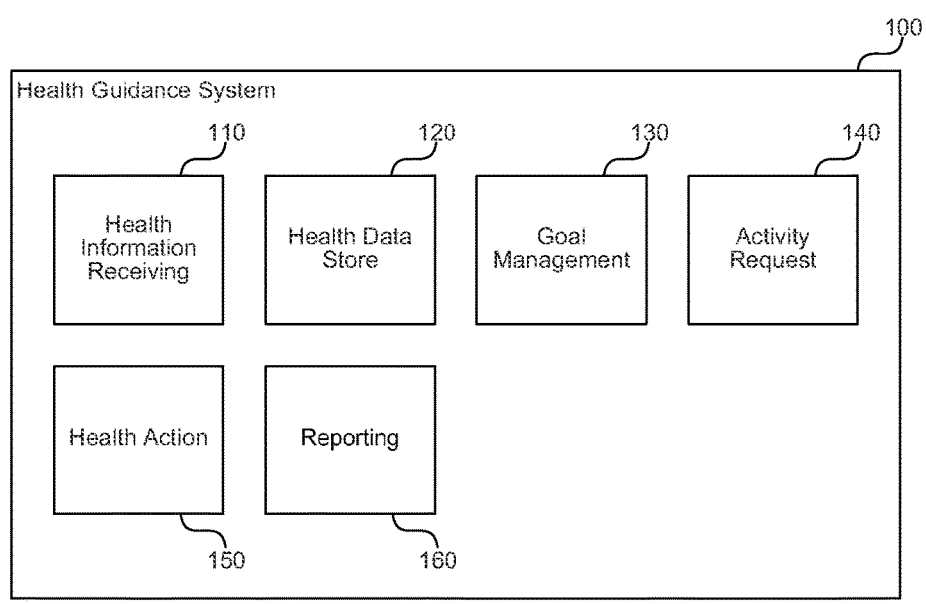
FIG. 1 is a block diagram that illustrates components of the health guidance system, in one embodiment.

FIG. 1 is a block diagram that illustrates components of the health guidance system, in one embodiment. The system 100 includes a health information receiving component 110, a health data store 120, a goal management component 130, an activity request component 140, a health action component 150, and a reporting component 160. Each of these components is described in further detail herein.

The health information receiving component 110 receives health information about a person from one or more devices associated with the person. For example, one device may include an electronic fork and activity monitoring device that provides a variety of information about the behavior of the person. As the person eats with the device it may collect information such as the weight of each bite, how many bites the person takes, the temperature of the food, a picture of the food, and so forth. As the person wears the device, it may collect information such as number of steps the person walks, the person's heart rate throughout the day, the person's global positioning system (GPS) location (e.g., home, gym, work, fast food restaurant), and so forth. Such devices may feed a large amount of information into the system 100 and the health information receiving component 110 stores the information in the health data store 120 for further processing. Additionally the health information receiving component 110 may receive health information about a product (e.g., sport article, food container, vegetable). For example, the system may receive from a cashier or a scanner information that a user is buying or wants to buy a product, and the system can recommend the product based on the user's monitored/received information such as: food contains good ingredients for user's cholesterol levels or sport article is good to train more efficiently based on user's weight and heart condition, or to prevent a user from buying a product based on the user's health-related information such as food should be avoided due to user's allergies or food needs to be avoided due to high content of corn syrup. Additionally the health information receiving component 110 may receive health information from a user's input (e.g., manually entered or selected by the user from a user interface). The health information receiving component 110 may receive health information such as the user's health-related goals. For example, a user may have entered on his user account website some health information, e.g., that his goal is to lose 10 pounds in 10 weeks, and the health information receiving component 110 receives this health information from which the system may infer additional health information, e.g., that the user is overweight and that his goals are challenging but achievable.

The health data store 120 stores health information about one or more users of the system 100. The health data store 120 may include files, a file system, a database, a storage area network (SAN), a cloud-based storage services, and numerous other paradigms for storing information. Because users are often sensitive to the storage of medical information, some information may be stored in a location under the control of the system while other information is stored separately under the user's control (e.g., on a personal USB drive). The health data store 120 keeps information over an extended period so that the other components of the system 100 can analyze the information to recognize trends, provide suggestions to the person, and provide anonymized reports to others (e.g., medical professionals, academic studies, and so forth). Additionally the health data store 120 may contain health information about products.

The goal management component 130 tracks one or more health-related goals of each person and processes received health information to determine progress toward those goals. The goal management component 130 may receive goals from one or more devices (e.g., health information receiving component 110 or an activity monitoring device) or from a person through a user interface (e.g., lose weight, extend life), and may suggest automatically generated goals based on the person's health information (e.g., suggest a need to lose weight or exercise more regularly). The goal management component 130 may include a user interface such as a web page or application dialog where a person can add, edit, remove, share, and manipulate goals in other ways. In addition, other people associated with the person may suggest goals, such as a physician suggesting lowering of cholesterol, a parent suggesting a healthy lifestyle for a child, and so forth. In addition, goals may be inferred by the system (e.g., the goal management component 130 can infer goals based on the health data store 120 or the health information receiving component 110). For example, the system may identify via its health data store 120 that a second user with similar health information than the one of the first user successfully lost weight by following specific patterns and goals; therefore the goal management component 130 may receive the goals of the second user and assign these goals to the first user. In some embodiments, the component 130 stores points in accordance with a point system that rewards a person for performing health activities (and potentially subtracts points for unhealthy activities). The person may use acquired points to gain access to other activities (e.g., earning one hour of watching television based on a day of healthy eating and exercise).

The activity request component 140 receives information about activities the person is about to perform that may relate to the person's health. For example, televisions may be designed to inform the system 100 whenever the person turns on the television, a computer may be programmed to inform the system 100 of the person's time spent sitting at the computer, a game console may provide information about time spent playing leisure games versus health games, a cashier may provide information about specific products the person intends to buy, and so forth. By informing the system 100 when activities begin, the activity request component 140 provides a mechanism for the system 100 to enforce health goals. For example, if a person has a goal that involves watching less television, then when the component 140 receives a request from a television, the component 140 can send the person an alert (e.g., a text message or email) or may even instruct the television not to allow the person to watch television or to display a message reminding the person of his or her health goal. These and other activity interactions by the system 100 to promote good health are described further herein.

The health action component 150 takes actions to promote progress of the person's health-related goals. The health action component 150 may interact with existing systems (e.g., email) as well as specialized health devices to promote the person's health. For example, the component 150 may email the person a daily reminder to exercise. As another example, the system may receive information that the user has eaten a lot of meat but few vegetables (e.g., from the electronic fork described herein), and suggest that the user eat more vegetables. As another example, the system may receive information that the user wants to wake up (e.g., from an alarm clock) and that his current sleep cycle phase is deep sleep (e.g., from motion sensors), and produce (e.g., through headphones) an appropriate binaural beat sequence to help the person wake up. The system may also inform devices about information to enforce the person's goals, such as setting a game console (e.g., Microsoft Xbox or Nintendo Wii) to allow the person to play fitness-related games, but not sedentary games. The system may also receive information that the user has bought too much junk food and not enough fruits and vegetables. Those of ordinary skill in the art will recognize a myriad of actions that the system 100 can take to promote good health. However, past systems have been unable to amass the comprehensive picture of the person's activities possible by the system 100 described herein, and thus the system 100 is able to be much more targeted and useful than past health-related systems.

The reporting component 160 produces reports identifying trends across users of the system 100. For example, a doctor or academic wanting to study daily activities of people of a certain weight range may use the system 100 to generate reports using anonymized data rolled up from multiple users of the system 100. As another example, drug companies, advertisers, or other companies may use the reporting component 160 to identify population trends or demographics that may be interested in specific products (e.g., an age group that exercises more frequently or eats more junk food), and so forth. In some embodiments, the system 100 may provide information about a specific person to other people identified by that person as having permission to view that information. For example, a person may grant his or her doctor permission to monitor the person's health and to modify goals to promote increased personal health.

The computing device on which the health guidance system is implemented may include a central processing unit, memory, input devices (e.g., keyboard and pointing devices), output devices (e.g., display devices), and storage devices (e.g., disk drives or other non-volatile storage media). The memory and storage devices are computer-readable storage media that may be encoded with computer-executable instructions (e.g., software) that implement or enable the system. In addition, the data structures and message structures may be stored or transmitted via a data transmission medium, such as a signal on a communication link. Various communication links may be used, such as the Internet, a local area network, a wide area network, a point-to-point dial-up connection, a cell phone network, and so on.

Embodiments of the system may be implemented in various operating environments that include personal computers, server computers, handheld or laptop devices, multiprocessor systems, microprocessor-based systems, programmable consumer electronics, digital cameras, network PCs, minicomputers, mainframe computers, distributed computing environments that include any of the above systems or devices, and so on. The computer systems may be cell phones, personal digital assistants, smart phones, personal computers, programmable consumer electronics, digital cameras, and so on.

The system may be described in the general context of computer-executable instructions, such as program modules, executed by one or more computers or other devices. Generally, program modules include routines, programs, objects, components, data structures, and so on that perform particular tasks or implement particular abstract data types. Typically, the functionality of the program modules may be combined or distributed as desired in various embodiments.

Figure 2:
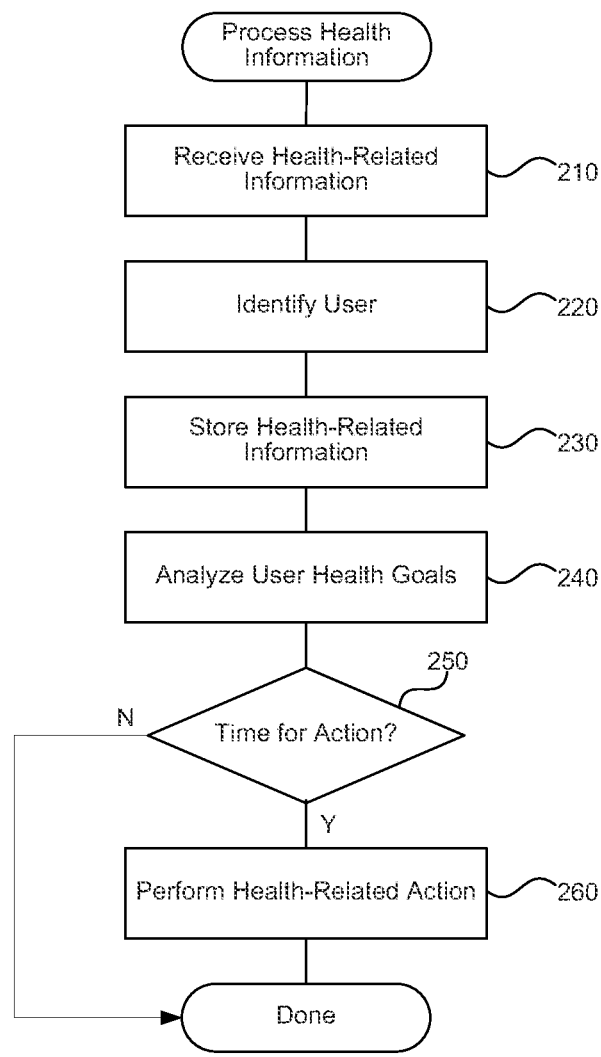
FIG. 2 is a flow diagram that illustrates processing of the system to process and act on health-related information, in one embodiment.

FIG. 2 is a flow diagram that illustrates processing of the system to process and act on health-related information, in one embodiment. Beginning in block 210, the system receives health-related information from one or more devices associated with the user. The system may receive numerous indications throughout the day with a variety of types of information. For example, a user's alarm clock may indicate when the user woke up, a location-based device may track the user's location, and an eating device may track the user's food intake. Continuing in block 220, the system identifies the user associated with the health information. For example, the device may provide a device identifier that the user previously registered with the system or the device may provide a user identifier that identifies the user to which the information applies. Users of the system may perform an initial registration process during which the system collects information about the user and the user registers devices that will be used to provide health-related information about the user.

Continuing in block 230, the system stores the health-related information in a data store. The data store may include a database that tracks many details about the user's activity over a long period to track trends on a daily, weekly, annual, or other basis. Continuing in block 240, the system analyzes one or more health goals associated with the user. For example, the system may generate goals based on the user's physical information (e.g., height, weight, and so forth), and may receive goals from the user or others that indicate specific needs of the user (e.g., reducing cholesterol, managing diabetes, avoiding stress, and so forth).

Continuing in decision block 250, if the system determines that it is time for action based on one of the user's health goals, then the system continues at block 260, else the system completes and waits for further information. The system may also operate in a loop, periodically analyzing goals to take action on time-based goals, such as going to bed by a particular hour, eating dinner within a specified period of the day, and so forth. Continuing in block 260, the system performs a health action based on the user's health-related information and health goals. For example, the system may send the user a notification (e.g., using a short message service (SMS) text message or instant message (IM)), send instructions to one or more devices associated with the user (e.g., an alarm clock, television, or game console), or perform other actions on the user's behalf (e.g., ordering delivery of a healthy meal, scheduling a massage appointment, and so forth).

Figure 3:
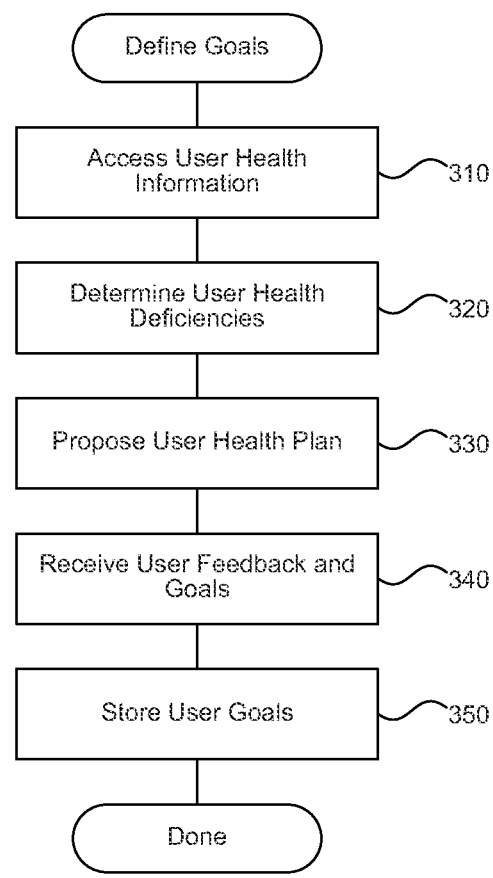
FIG. 3 is a flow diagram that illustrates processing of the goal management component to receive and generate user health goals, in one embodiment.

FIG. 3 is a flow diagram that illustrates processing of the goal management component to receive and generate user health goals, in one embodiment. Beginning in block 310, the component accesses user health information from a data store. For example, the component may access information stored in the health data store that was previously received from one or more devices associated with the user or entered manually by the user. Continuing in block 320, the component determines user health deficiencies by analyzing the accessed health information. The system may receive models from health professionals or others that describe healthy conditions for users, including proper height/weight ratios, sleep patterns, healthy eating guidelines, and so forth. The system may also receive specific information about the user from the user or the user's doctor that indicates, for example, whether the user has diabetes or other conditions that may modify the appropriate healthy activities for the user. Based on this information, the component determines areas where the user falls outside of the provided models or the suggested guidelines.

Continuing in block 330, the component proposes a health plan to the user for promoting a healthy lifestyle. For example, the component may suggest a level of daily exercise, a recommended caloric intake, recommended activity times (e.g., for sleeping, exercising, or eating), and so forth. The plan may also include specific device recommendations, such as recommending a limit to daily television watching or recommending a duration of use of an exercise machine accessible to the user. Continuing in block 340, the component receives user feedback and individual goals of the user. The user may view the health plan proposed by the component and identify other health goals specific to the user, such as being ready to run a marathon by a specified time or being able to climb a particular mountain. The system can help the user to achieve a variety of health goals. The user may also modify the recommendations of the system, such as by raising or lowering a target weight or changing a period for achieving particular goals.

Continuing in block 350, the component stores the user's health goals in a data store for subsequent use by a system for enforcing the goals. For example, the component may store the goals in the same database as the user's received health information and may provide the goals to the health action component to program the devices in the person's life to promote the person's health goals.

Figure 4:
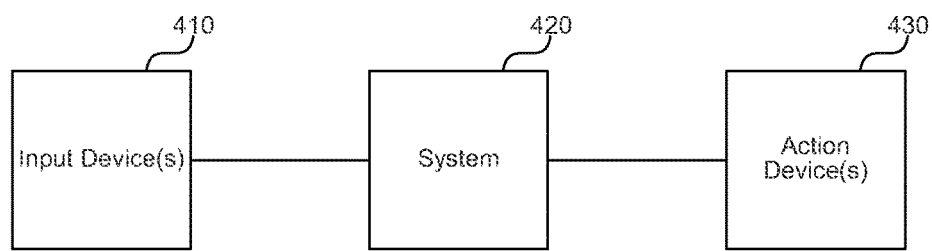
FIG. 4 is a block diagram that illustrates a typical environment of the system, in one embodiment.

FIG. 4 is a block diagram that illustrates a typical environment of the system, in one embodiment. The system 420 receives information from one or more input devices 410, which may include an electronic utensil, computer, alarm clock, various health monitoring devices, and so forth. The system 420 provides instructions to one or more action devices 430 that influence the user's behavior. The action devices 430 may include MP3 players, a cashier or electronic store, phones, computers, televisions, game consoles, external locks, and even other people (e.g., by emailing the user's goals). Thereafter, since the action devices 430 may affect directly or indirectly the input devices 410, a feedback loop may be created from the action devices 430 to the input devices 410, allowing the system to readjust accordingly based on the action feedback.

The health guidance system can operate with many types of devices that have a positive or negative direct or indirect impact on a user's health, wellness, fitness, activities, and non-activities, such as a game console, a television, a computer, a phone, a cashier, a music player, a video player, and so on. As one example, an eating device can be used with the system that is embedded in an object shaped like an eating utensil (e.g., a fork). The eating device monitors behaviors, state of mind, and captures a large amount of information about the user in a database. Many statistics can be inferred from the information that are built on the user's monitored data, the user's input, the user's social group interactions, and so forth. Extracted statistics can validate, refine, or open new research in the field of weight loss and wellness. For example, one can infer about the right eating patterns based on conditions, or an amount of exercise one has to do based on its users' conditions (e.g., weight, age, race, gender, health issues, brain activity, mind states, medical issues). Typically, research or studies are limited to a restrained number of patients and therefore most studies do not take into account the varieties of gender, race, conditions, and the like that can impact in one way or another the output of any study.

The health guidance system database also serves as a benchmark for studies to validate studies and to analyze all the variations based on users' conditions. The high number and variety of patients in the system creates a wealth of information that may revolutionize the health industry, such as specifically related to weight loss, clinical trials, and studies. Moreover, the system provides an accurate way to generate statistics on overall trends (e.g., 60% of people are now partnering to weight loss which represents a 12% increase, 20% of people lose 10% of their weight in the first 6 weeks, 20% of them gain everything back after 6 months, and so on), which can themselves be broken down based on users' conditions (gender, age, and so forth).

In some embodiments, the health guidance system provides a concept of grades ("points"). The grade corresponds to the amount of goals the user has currently achieved based on real-time measurement. A high grade corresponds to the daily desired or target goals defined manually or automatically by the user, a coach, a physician, or the like. There are wellness sub-grades provided for each area of health (e.g., diet, exercise, and so on). Areas can be eating (grade/goals can be given based on number of calories, speed of eating, time between meals, quality of food eaten, and all other eating related features), exercise (e.g., number of calories, distance, stairs), sleep (e.g., amount of sleep, quality of sleep), environment (amount of TV viewing, game console playing), shopping (buying healthy food, buying seasonal fruits, no soda or pops), and so forth. The system also computes an overall wellness grade based on the different sub-grades (may be simple average or weighted average or any decision-making or statistical operation).

The information collected is sufficient to obtain an overall energy balance since the system captures both the energy intake and expenditure (even if estimated). Therefore, the system is able during the day to indicate times someone has to eat, if they have to eat more or less, signal while eating if they have to stop eating or continue, signal while exercising to do more exercise or stop exercising, and so forth. All of this allows the user to reach the right balance between energy intake and outtake. In short, since the system can infer what the user is doing (eating, exercising, sleeping, or other activity components) and the amount the user has done in past days and the current day, the system can regulate on the fly, advise on the fly, (on the fly and/or spread over the day or days or weeks) to obtain the correct balance to achieve healthy living.

In some embodiments, the health guidance system receives and integrates wellness profiles to manage user goals. For example, the system can use a weight loss management profile to set device parameters or provide user feedback. Profiles can be sent from social groups, a personal coach, physicians, a digital coach (pre-registered or automatically generated profiles based on heath data patient), and so forth. For example, individuals may identify themselves in support groups (via software, online social network, and so on), so that obese people that went through a gastric bypass surgery (aka bariatric surgery) can add a flag that identifies them as such so that they can create or join a "working group" to support them after the surgery or to automatically receive recommended eating habit patterns. Most surgeons have support groups in place to assist with short-term and long-term questions and needs. Most bariatric surgeons who frequently perform weight loss surgery explain that ongoing post-surgical support helps produce the greatest level of success for their patients.

In some embodiments, the health guidance system receives information from one or more cameras. For example, a camera can automatically take a picture of 1) what you are eating at the detection of bite for later picture assessment or simple user review and/or 2) the face of the person eating for security or accountability reasons. A picture of the user's plate or food can be used to perform calorie assessment (e.g., 300 calories), nutriments assessment (e.g., corn syrup, junk food, processed food, healthy food, not enough fruits/vegetables), and quantity assessment (e.g. too much meat and not enough vegetables, too much sauce or ketchup). A picture of the user's face can be used for identification of the right user for security reasons (e.g., for incentive programs such as insurance, corporate, schools, governments, who want to make sure that it is the right person using the utensil or device), identification of the user for familial reasons (e.g., parents who want to make sure it is their kid that actually uses the system), or for benefits.

One study showed that dieters photographing everything they eat encouraged them to change their diet. When the volunteers were later quizzed, the photo diary appeared more effective at encouraging them to change their eating habits to more healthy alternatives. The photographs also acted as a powerful reminder of any snacking binges the researchers found. The researchers who carried out the study found that written food diaries (compared to pictures) were often filled in hours after the meal and were not as powerful in creating an impression of how much food had been consumed.

The system can process pictures internally or send the pictures out to a processing center that analyzes pictures and provides feedback based on identified food and quantities.

The processing mechanism may employ an automated recognition mechanism, specially trained humans, or simple logic in offline software.

The camera can also be used to detect or verify information that is difficult to obtain through other sensors. For example, although an electronic eating utensil may attempt to measure bite count (e.g., through a pressure switch or light beam), a camera can be used to verify the count (by tracking jaw movement). After a meal, users may add supplemental information associated with the picture that is sent to the system for processing. For example, the information may include further details about the type and source of the food. Another study showed that those who kept daily food records lost double the amount of weight of those who kept no food records.

In some embodiments, the health guidance system reminds a user about a previous meal at the start of a current meal. For example, when the system receives information from a device that a meal has started (e.g., by detecting a first bite through an electronic eating utensil), then the system may ask a question about the previous meal and wait for a reply. This helps the user remember the meal and may remind the user that, for example, the user had a high calorie lunch and therefore should prefer a lower calorie dinner. The system can ask the user to answer questions such as the last meal length, the meal quality (junk food, healthy), or any information that was entered manually or automatically during the last meal. Furthermore, the system can ask the user to select in a picture database (can be presented as a slideshow) the picture corresponding to their last meal to help them focus and remember their last meal. Researchers believe prior memory association between sensory cues and post-ingestion consequences of eating might trigger a response to eat less.

In some embodiments, the health guidance system provides guidance to the user during meals. For example, based on stress or health detection during a meal (e.g., manually through pre-set profiles or automatically through a detection mechanism such as heart beat, brain waves, and so forth), the system can ask the user to breath or relax 1) between two bites and/or 2) before the meal starts or after the first bite is detected. Researchers have shown that each session of intellectual work uses only three calories more than the rest period. However, despite the low energy cost of mental work, students spontaneously consumed 203 more calories after summarizing a text and 253 more calories after the computer tests. This represents a 23.6% and 29.4% increase, respectively, compared with the rest period.

In some embodiments, the health guidance system provides suggestions to the user throughout the day. For example, at any time during the day and based on current monitored activity or length of time since a previous event, the system can alert the user and provide routine exercise or activity suggestions for good health (such as stretching—like in airplanes—or drinking a half pint of water). This allows the user to prescribed exercises or routines from physicians, nutritionists, personal trainer, or preset profiles.

In some embodiments, the health guidance system stores additional records related to the user's health information. Since the system already contains health and wellness information about the user the system can be used to store additional data such as medical records and social security insurance details. Storing medical records (with encryption) allows the system to deliver easily and appropriately information to a physician, nutritionist, personal trainer, and so forth. Since the system is ubiquitous in the user's life, the user may use the system to store not only monitored or controlled information but also any health record information from a patient. Data may be encrypted for security purposes and only read by authorized physicians.

This solution is useful for government as they can add incentives to preventive health actions and more importantly audit users that accept to participate in such incentive programs. Most governments are interested in leveraging preventive healthcare.

In coordination with a device carried by a person that is in contact with the system, the system allows any person to carry on them their records at all times and to be able to access or provide the right information when needed. This can be beneficial, for example, if someone is found on the ground after an accident when first aid needs to make the right actions (based on the person's medical records: allergies, past surgeries, current medication, and so on). A simple access to the device can provide all the correct information and may save lives. The system may include an emergency password accessible only to selected health professionals for emergency reasons.

The system can also store insurance information and act as an insurance reimbursement card to 1) avoid fraud and, after pertinent authentication, 2) allow direct reimbursement or 3) allow identification of the remaining amount (complete/partial payment of the medical treatment, medication, or service) to be paid by user directly or indirectly to a pharmacist, physician or other health-related services. The system acts as an authentication and validation card and contains all of a user's social security or other insurance details. For additional security, the insurance information may include a picture of the user for additional security. The physician who uses the device can see the ID picture and check visually if the person is the one on the picture, compare the ID picture with a picture in a national ID card database, compare automatically the ID picture with an online/offline 3rd party security facial verification database (such as the one for passport identification that custom use when crossing borders), and so forth. Optionally a fingerprint device can be integrated as well as other authentication means.

If a person seeks medical treatment, he may need to pay before or at the end of each consultation, and later receive reimbursement from the social security system (and your voluntary/private insurer if you have one). Furthermore, hospitals, pharmacists, and physicians are using ID cards to identify their patients before providing care, which leads to numerous frauds and higher costs to healthcare due to easy access to fake ID cards. Here a device is presented to the doctor who can read the device enabling the user to securely identify him and optionally obtain direct reimbursement from the insurance fund, rather than having to go through additional and less secure steps. The user can also use the device in a drugstore for any prescription reimbursements. If he has voluntary/private insurance, the system will also (normally) pay directly into the user's bank account that part of the charge that is not fully reimbursable from the social security system, subject to the conditions of cover.

In some embodiments, the health guidance system receives information about a user's brain wave activity. A device carried by the user can monitor at any time of day and night the current level of the user's brain electrical activities (aka brainwaves) or state of mind or conditions (via sensors—they can be, e.g., unsophisticated sensors such as heart beat or motion sensors, audio sensors or video sensors, or more sophisticated ones such as EEG or any type of MRI such as FMRI—or any combination of the above for better measurements). Based on this information, the system may invoke the device to generate new brain electrical activities, new state of mind, or a new condition (via, e.g., producing brainwaves frequencies, beats (e.g., binaural or rhythmic), subliminal messages (audio or video), suggestion messages (audio or video), hypnotic sessions/messages (audio or video), or the like, or via injecting electric current (e.g., using electrodes), photo-activation methods (e.g., light-emitting prosthetics, laser or light), fluid, substance, or the like—or any combination of the above for more powerful efficacy). This allows the system to regulate and guide the user to a desired/targeted brainwave level that is manually setup, or based on a pre-programmed schedule, profile, or needs (eating, sleeping, working, waking up), or automatically generated by a personalized program. The generation of the information to change the state of mind can be done gradually from an initial brain activity (e.g., the monitored brain activity) to the desired/targeted brain activity. The system may use devices registered by the user, such as a television or MP3 player to help guide the user to a desired state (e.g., calming down before sleeping).

This may benefit individuals with Parkinson's disease by reducing beta wave activity when a Parkinson movement (characterized by tremor and slowed movements) is detected by sensors (any motion sensor such as accelerometers or video sensors can be used). As beta activity is associated with slow movement, the system may remove or reduce beta waves (responsible for slow movements) and generate any output stated above, for example, gamma waves to avoid symptoms and maybe slowly remove disease. Similar logic works with other conditions or diseases such as chorea, dystonia, and ADHD.

A known and efficient way to generate brainwaves is through binaural (stereophonic) beats, such as through headphones. Rhythmic beats are also a known way to generate brainwaves without headphones. While there are other methods (e.g., goggles that flash light at particular frequencies), the two above are the most common. Brainwaves affect mood, focus, body healing, and many other health factors. For example, one study demonstrated how the drumbeats found in the rituals of various cultures beat at a steady rate of 4.5 beats per second, inducing a trance-like state in listeners. This trance-like state is a result of the brain's shift into a 4.5-beats-per-second brainwave pattern, a low Theta brainwave state.

Based on the information received by the system, the system provides the adequate output or desired state of mind (e.g., using brainwave generation sequence, subliminal messages, hypnotic messages or others) via one or multiple interfaces (such as speakers, headphone, television, display monitor, projector, or other means) to get rid of bad habits, bad conditions, or bad behaviors and/or to enforce good habits or good behaviors. The system automatically controls and regulates audio and/or video generators (such as, e.g., a music beat generator, brain wave frequency generator, suggestion generator, hypnotic message generator, and/or subliminal message generator) based on environment, alerts, issues, programs, and so forth. This may be done internally by incorporating common music and/or video players together with an audio and/or video frame generator into a device carried by the user, or externally by controlling external players and generators, or through both internal and external methods.

Modifying states of mind via, e.g., subliminal, suggestion and hypnotic messages, takes time and rigorous action/listening/viewing with specific repetitive patterns to profoundly influence a user. The system automatically controls the repetitive pattern of the generators to ensure an appropriate effect on the user based on the user's monitored actions and dedication. For example, once the system receives the information that the user is eating too fast and too much, the system starts a 3-month program with subliminal messages targeting the bad behaviors, and based on the user monitored actions and commitment the system can accordingly add or subtract listening time to affect optimally the user.

In some embodiments, the system may fuse an audio track with health benefits with an audio track that the user is already listening to (e.g., through an MP3 player). The system can perform mixing on the fly (both audio tracks are mixed on the fly—that is, e.g., one can select any music from his player or no music, and the generator will generate automatically in the background the right frequencies, beats, audio/video messages, and so on) or pre-recorded (that is the user can select directly the right pre-mixed music/video that already contain the right frequencies, beats, audio/video messages, and so forth). Therefore, the system may control one or more players at the same time including at least one generator.

In some embodiments, the system may insert video frames with health-related benefits on top of video frames that the user is already viewing (e.g., through a computer monitor, game console monitor, or television that, e.g., display the user interface video on the computer screen or show recorded or live video frames such as a DVD, television channel, video game, or webcam-enabled chat). The system can perform mixing on the fly (health-related video frames are mixed/inserted on the fly inside the original displayed video—that is, e.g., one can select any TV channel or use its computer monitor, and the generator will generate automatically in the background the right subliminal messages, and so on) or pre-recorded (that is the displayed video is the pre-mixed video that already contains the right subliminal messages, and so forth).

As an example of the above, the system may help the user wake up by gradually modifying the user's brainwaves shortly before the user's alarm is schedule to sound. For example, if the user plans to wake up at 6:00 A.M. then at 5:00 A.M. the system may start to trigger gradually the following different states: Delta (deep sleep), to Theta (drowsiness), to Alpha (relaxed but alert), and finally to Beta (highly alert and focused). As another example, the system may help a user reach a relaxed but alert state before eating in order to enhance digestion. As another example, the system may play subliminal messages that help the user lose weight and binaural beats on top of the user's music when the user uses its music player and this at least 30 min daily during 6 months. As another example, the system may display on the user's computer monitor subliminal messages that help the user focus while the user works (e.g., inserting one health-related video frame each second that lasts $\frac{1}{30}^{th}$ of a second on the computer display) or that help the user fix some bad behaviors while the user views a movie on his television (e.g., inserting one health-related video frame every 29 movie frames).

In some embodiments, the system may receive information that the user is shopping (e.g., via an automatic cashier message, e-commerce website message or user input). The system may control in real-time or not the shopping habits of the user, based on the products/groceries that the user selects, based on the health-related information of the user, based on the health-related information of the products/groceries, or based on any combination of the foregoing. Therefore, the system may, e.g., appropriately grant or prevent the buying of the product directly at the manual or automatic cashier, inform the user of the healthy or unhealthy choice and the reason why, recommend alterative products/groceries to replace products selected by the user that were tagged as non-healthy, suggest to the user products/groceries that would be beneficial for his health, suggest a list of products/groceries and associated recipes to prepare health-tailored meals based, e.g., on the user's activities, tastes and/or health, and/or record the buying patter for later review by the user or by authorized persons (e.g., physician, nutritionist, insurance, or the like). For example, a product can be classified as bad or not healthy or not recommended if, e.g., it is too calorific, contains too much sugar, includes high percentage of corn syrup, is genetically modified, or the vegetables or fruits are not seasonal.

In some embodiments, the health guidance system controls the timing during which a user can perform certain activities. For example, the system may not allow the user to shop for groceries when it is time to eat or an interval of time before eating. Doing shopping while hungry will make the user make bad choices even if she knows what is healthy. Doing shopping while fed allows the user to disregard bad food more easily and buy healthy food.

The control of third party devices can be made via different data links. The data links can be based on wired communication, such as PS/2, USB, FireWire, DVI, HDMI, Serial, Parallel, and the like, or on wireless communication, such as IR, RF, Bluetooth, WLAN, WWAN, 3G, and the like, or various combinations of wired and wireless communication. The data links may be enabled manually, such as by plugging in a USB cable, or automatically, such as by connecting automatically when in the proximity of a Bluetooth transmitter. In the case of wireless data links, the data link unit may include an antenna to receive and transmit data or signals.

In some embodiments, the health guidance system provides user groups and access level controls. For example, a parent and child may be users in a group and the parent may have authority to modify or override system behavior for the child. For example, the parent may prevent the child from playing video games until health goals are met, but may also override such goals, such as when playing together.

In some embodiments, the system provides information to connect users. For example, the system may identify a user that historically had similar goals to a second user's current goals, where the first user successfully achieve his goals. This may allow the second user to view anonymous data about the first user (e.g., how much he exercised, what he ate, and so forth), to help the second user achieve the goal. In addition, the system may provide a mechanism for the users to connect (e.g., through an invitation) as friends and may offer incentives for users to act as coaches or mentors for other users. In this way, users of the system can increase one another's health and support each other in achieving a healthy lifestyle.

From the foregoing, it will be appreciated that specific embodiments of the health guidance system have been described herein for purposes of illustration, but that various modifications may be made without deviating from the spirit and scope of the invention. For example, although some device types that can be used with the system have been provided in examples, numerous other existing and future devices can be used, such as refrigerator locks (e.g., only opening at meal time), smart phones (e.g., only allowing leisure calls when exercise goals are met), and so forth. Accordingly, the invention is not limited except as by the appended claims.

We claim:

1. A computer-implemented method for promoting human health, the method comprising:
    performing the following steps by at least one processor;
    establishing a communication link between the processor, an eating monitoring device monitoring eating of a user, and an action device used by the user, wherein the processor controls ability of the user to access functionality of the action device selected from the group consisting of one or more of (1) playing a videogame, (2) watching a video display of the action device, and (3) watching television;
    receiving health-related information of the user from the eating monitoring device;
    receiving one or more thresholds associated with health-related goals of the user, wherein the type of the health-related information and the type of the one or more thresholds are selected from the group consisting of one or more of: (1) speed of eating, (2) number of bites taken by user, (3) time between meals, (4) meal length, (5) weight of food eaten by user, (6) calories of food eaten by the user, (7) quantity of food eaten by the user, (8) quality of food eaten by the user, (9) characteristics of food eaten by the user, and (10) ingredients of food eaten by the user;
    receiving action-related information from the action device, wherein the action-related information comprises information of functionality of the action device utilized by the user; and
    implementing a feedback loop comprising: (a) continuously monitoring the received action-related information of the action device, (b) comparing the health-related information with at least one of the corresponding one or more thresholds, and (c) determining whether at least one of the compared thresholds is met, and (d) based on the determination that the at least one of the compared thresholds is met, sending at least one computer-executable instruction to the action device to allow or remove access to the functionality of the action device.

2. The method of claim 1, wherein the action-related information corresponds to one or more of on-off status of the action device, type of videogame, video or television program and duration of the action.

3. The method of claim 1, wherein the eating monitoring device is also a physical activity monitoring device.

4. The method of claim 1, wherein the method further comprises establishing a communication link between a physical activity monitoring device monitoring the user and the action device; receiving first health-related information corresponding to the user from the physical activity monitoring device, wherein the first health-related information is selected from the group consisting of one or more of calories out, distance and number of steps or stairs taken by the user.

5. The method of claim 1, wherein the method further comprises establishing a communication link between a sleep monitoring device monitoring the user and the action device; receiving second health-related information corresponding to the user from the sleep monitoring device.

6. The method of claim 1, wherein the method further comprises sending a notification to the user related to at least one of the one or more health-related goals, the health-related information and the action-related information based on the comparison results.

7. The method of claim 1, wherein the action device is a video display or a television.

8. The method of claim 1, wherein the action is watching a video display or television, and wherein allowing or removing access to a functionality of the action device controls one or more of: the type of video output, the type of television program, the duration of video output, and the duration of television program.

9. The method of claim 1, wherein the action device is a video game console.

10. The method of claim 1, wherein the action is playing video game, and wherein allowing or removing access to a functionality of the action device controls one or more of: the type of video game and the duration of video game.

11. The method of claim 1, wherein at least one of the health-related information and the action-related information includes information that is obtained from one or more cameras.

12. The method of claim 1, wherein at least one of the health-related information and the action-related information includes information obtained from monitoring the user's brain waves.

13. The method of claim 1, wherein one or more of the health-related information, the action-related information and the computer-executable instruction is sent or received through at least one wireless communication link.

14. A computer system for encouraging healthy living, the system comprising:
a health information receiving component configured to receive health-related information corresponding to one or more users from one or more eating monitoring devices corresponding to each user, wherein the type of the health-related information is selected from the group consisting of one or more of (1) calories of food eaten by the user, (2) quantity of food eaten by the user, (3) quality of food eaten by the user, (4) characteristics of food eaten by the user, (5) ingredients of food eaten by the user, (6) speed of eating, (7) number of bites taken by user, (8) time between meals, and (9) weight of food eaten by user;
a health data store configured to store health-related information about the one or more users;
a goal management component configured to receive and track one or more thresholds corresponding to health-related goals of each user and process the received health-related information to determine whether the one or more thresholds is met;
an activity request component configured to receive action-related information from one or more action devices corresponding to each user, the activity request component controlling ability of the user to access functionality of the action device, wherein the functionality is selected from the group consisting of one or more of: shopping, playing video game, watching video display, and watching television, wherein the action-related information selected from the group consisting of one or more of: (1) an on-off status of the action device, (2) a duration of the use of the functionality, (3) a type of video game displayed or implemented by the action device, (4) a type of video display output displayed or implemented by the action device, and (5) a type of television program displayed or implemented by the action device;
a health action component configured to take actions to promote user's progress towards the user's health-related goals by implementing a feedback loop comprising: (i) continuously monitoring the received action-related information of the action device, (ii) comparing the health-related information with at least one of the one or more thresholds, and (iii) determining whether at least one of the one or more thresholds is met, and (iv) based on the determination that at least one of the one or more thresholds is met, sending at least one computer-executable instruction to the action device to allow or remove access to the functionality of the action device to control at least one of: duration of the action, what can be purchased by the user, what type of videogame can be played by the user, what type of video display output can be watched by the user, or what type of television program can be watched by the user; and
a processor and memory configured to execute software instructions, wherein the software instructions implement the health information receiving component, the health data store, the goal management component, the activity request component and the health action component.

15. The system of claim 14 wherein the eating monitoring device is used during eating as a utensil to consume food.

16. The system of claim 14 wherein the system is further configured to manage user groups and provide access level controls.

17. A computer-implemented method for promoting human health, the method comprising:
performing the following steps by at least one processor;
establishing a communication link between the processor, an eating monitoring device monitoring a user and an action device used by the user, wherein the the processor controls ability of the user to access functionality of the action device selected from the group consisting of one or more of (1) eating, (2) shopping, (3) playing video game, (4) watching a video display of the action device and (5) watching television;
receiving health-related information of the user from the eating monitoring device, wherein the health-related information is at least based on data monitored by the eating monitoring device, and wherein the type of the health-related information is selected from the group consisting of one or more of: (1) speed of eating, (2) number of bites taken by user, (3) time between meals, (4) meal length, (5) weight of food eaten by user, (6) calories of food eaten by the user, (7) quantity of food eaten by the user, (8) quality of food eaten by the user, (9) characteristics of food eaten by the user, and (10) ingredients of food eaten by the user;
receiving one or more thresholds associated with health-related goals of the user, wherein the type of the health-related information and the type of the one or more thresholds correspond to one another;
receiving action-related information from the action device, wherein the action-related information comprises information of functionality of the action device utilized by the user; and
implementing a feedback loop comprising: (i) continuously monitoring the received action-related information of the action device, (ii) comparing the health-related information with at least one of the corresponding one or more thresholds, (iii) determining whether at least one of the one or more thresholds is met, and (iv) based on the determination that at least one of the one or more thresholds is met, sending at least one computer-executable instruction to the action device to allow or remove access to the functionality of the action device to control at least one of: duration of the action, what can be purchased by the user, what can be eaten by the user, what type of videogame can be played by the user, what type of video display output can be watched by the user, or what type of television program can be watched by the user.

18. The method of claim 17 further comprising authenticating or identifying the user.

19. The method of claim 17, wherein the eating monitoring device is also a physical activity monitoring device, and wherein the type of the health-related information is further selected from the group consisting of one or more of: type of activity, timing of activity, quality of activity, quantity of activity, location of activity, duration of activity, number of steps, number of stairs the user takes, calories, distance, energy intake, energy expenditure, and energy balance.

* * * * *